United States Patent [19]
Ashida et al.

[11] Patent Number: 5,994,324
[45] Date of Patent: Nov. 30, 1999

[54] WATER-SOLUBLE VITAMIN COMPOSITION HAVING EXCELLENT TABLET PROPERTIES AND PROCESS FOR PRODUCTION THEREOF

[75] Inventors: Hiroshi Ashida, Nishinomiya; Daisuke Izutsu, Souraku; Akio Yamashita, Amagasaki, all of Japan

[73] Assignee: Takeda Chemical Industries, Ltd., Osaka, Japan

[21] Appl. No.: 08/793,748

[22] PCT Filed: Oct. 23, 1996

[86] PCT No.: PCT/JP96/03079

§ 371 Date: Mar. 13, 1997

§ 102(e) Date: Mar. 13, 1997

[87] PCT Pub. No.: WO98/09624

PCT Pub. Date: Mar. 12, 1998

[30] Foreign Application Priority Data

Sep. 5, 1996 [JP] Japan ................................. 8-234940

[51] Int. Cl.⁶ ..................... A61K 31/715; A61K 31/34; A61K 31/045
[52] U.S. Cl. ............... 514/57; 514/23; 514/53; 514/58; 514/474; 514/738
[58] Field of Search ............... 514/25, 53, 54, 514/58, 57, 23, 738, 474; 549/315

[56] References Cited

U.S. PATENT DOCUMENTS

| | | | |
|---|---|---|---|
| 3,293,132 | 12/1966 | Stoyle et al. | 167/82 |
| 4,036,948 | 7/1977 | Kitamori et al. | 424/32 |
| 4,372,968 | 2/1983 | Kitamori et al. | 424/280 |
| 4,800,086 | 1/1989 | Buehler et al. | 424/497 |
| 5,000,888 | 3/1991 | Kilbride, Jr. et al. | 264/7 |
| 5,080,908 | 1/1992 | Ono et al. | 424/499 |
| 5,236,920 | 8/1993 | Kilbride, Jr. et al. | 514/251 |
| 5,254,551 | 10/1993 | Kirk et al. | 514/251 |

FOREIGN PATENT DOCUMENTS

| | | |
|---|---|---|
| 49143 | 4/1982 | European Pat. Off. . |
| 178138 | 4/1986 | European Pat. Off. . |
| 219276 | 4/1987 | European Pat. Off. . |
| 2616078 | 2/1977 | Germany . |
| 1 564 687 | 4/1980 | Germany . |
| B 45-23159 | 8/1970 | Japan . |
| 51-14522 | 12/1976 | Japan . |
| 55-055112 | 4/1980 | Japan . |
| 0 049 143 | 7/1982 | Japan . |
| 63-005030 | 1/1988 | Japan . |
| 1165519 | 6/1989 | Japan . |
| 1296953 | 11/1989 | Japan . |
| 2282323 | 11/1990 | Japan . |
| 6902999 | 11/1969 | South Africa . |

OTHER PUBLICATIONS

Shesky et al. *Pharm. Tech.,* vol. 19(10): 98, 100, 102, 104, 106, 108, 110, 112. Abstract Only, 1995.

Ansel et al. *Pharmaceutical Dosage Forms and Drug Delivery System,* Williams & Wilkins, pp. 192–202, 1995.

*Primary Examiner*—Howard C. Lee
*Attorney, Agent, or Firm*—Foley & Lardner

[57] ABSTRACT

There is disclosed a water-soluble vitamin composition which containing about 90 to 99.8% by weight of a water-soluble vitamin, a polymer binder and at least one additive selected from the group consisting of monosaccharides, disaccharides, sugar alcohols, dextrin and organic acids, which can provide a tablet having high mechanical strength (hardness) with less compression problem and easy disintegration, upon compression. A process for producing the composition is also disclosed.

4 Claims, No Drawings

WATER-SOLUBLE VITAMIN COMPOSITION HAVING EXCELLENT TABLET PROPERTIES AND PROCESS FOR PRODUCTION THEREOF

FIELD OF THE INVENTION

The present invention relates to a water-soluble vitamin composition and a process for production thereof.

BACKGROUND OF THE INVENTION

For producing tablets containing water-soluble vitamins such as L-ascorbic acid as an active component, a large amount of a binder is required, which limits a L-ascorbic acid content. Many activities have been attempted to produce tablets having a high L-ascorbic acid content and tablets having high mechanical strength (hardness).

For example, in U.S. Pat. No. 3,453,368, 85 to 95% by weight of L-ascorbic acid is mixed with 5 to 15% by weight of modified starch and the mixture is subjected to wet kneading. Then, the resultant mixture is granulated and dried to obtain granules containing L-ascorbic acid, mixed with a lubricant and compressed to obtain tablets containing L-ascorbic acid.

However, according to this method, it is difficult to obtain homogenous granules and fluidity of the granules is not satisfactory. Moreover, tablets prepared using the granules have insufficient mechanical strength (hardness).

In general, tablets need certain mechanical strength (hardness) to prevent breakage and wear during production and marketing steps and use. Then, activities have been attempted to investigate production processes, various excipients, binders, disintegrators and lubricants.

JP-B 58-403 discloses a process for production of L-ascorbic acid granules having excellent compressibility which comprises fluidizing L-ascorbic acid powder which can pass through a 200 mesh sieve in a fluidized bed granulator, while spray-coating the granules with a solution containing about 1 to about 10% by weight of a binder such as a water-soluble, organic solvent-soluble cellulose material to obtain granules containing about 2 to about 4% by weight of the binder. This patent also discloses a process for producing a pharmaceutical preparation which comprises mixing a lubricant with the above-obtained L-ascorbic acid granules and compressing the resultant mixture into a tablet.

JP-B 61-21526 discloses granules for tablets having a specific distribution of particle size comprising about 98:5 to 99.5% by weight (dry matter) of sodium L-ascorbate and a binder such as a water-soluble, organic solvent-soluble as cellulose material, and a tablet using the granules.

JP-B 5-66928 discloses granules for tablets having a specific distribution of particle size, wherein soluble polyvinyl pyrrolidone and ascorbic acid are used, and there is disclosed that a tablet having a high disintegration rate is obtained.

OBJECTS OF THE INVENTION

Strength of tablets can be improved to some extent according to the above conventional techniques for improving mechanical strength (hardness) of tablets. However, it is yet insufficient. Moreover, tablets having relatively higher mechanical strength (hardness) tend to have longer disintegration time.

Then, an object of the present invention is to provide a water-soluble vitamin composition having an excellent tablet properties from which a tablet having higher mechanical strength (hardness) in comparison with conventional tablets and having excellent disintegration properties, i.e. having a high disintegration rate can be obtained. The present invention also provides a process for production of the composition.

SUMMARY OF THE INVENTION

In view of the above circumstances, the present inventors have studies intensively. As a result, the present inventors have found that compression molding properties can be improved by using a certain additive without increasing the amount of a binder and that, although a concentration of a spray solution for granulation becomes higher, its viscosity does not increase, thereby granulation can be done in a period almost same as that prior to addition of the additive. The present inventors have further studied and have completed the present invention.

That is, the present invention provides a water-soluble vitamin composition which comprises about 90 to 99.8% by weight of a water-soluble vitamin, a polymer binder, and at least one additive selected from the group consisting of monosaccharides, disaccharides, sugar alcohols, dextrin, and organic acids.

The present invention also provides a process for producing the water-soluble vitamin composition of the present invention which comprises carrying out granulation while coating the water-soluble vitamin with a solution of the polymer binder. In the process of the present invention, granulation can be carried out while coating a mixture of the water-soluble vitamin and the additive with a solution of the polymer binder, or granulation can be carried out while coating the water-soluble vitamin with a solution of the polymer binder and the additive. As for granulation methods, per se known methods such as fluidized bed granulation, spray drying, kneading and rolling pan granulation can be employed. In particular, a fluidized bed granulation method is preferred.

The composition of the present invention can be mixed with, for example, a known lubricant ant the like to obtain a tablet by a conventional method. According to the present invention, a tablet having a higher water-soluble vitamin content and having excellent tablet properties can be obtained. Then, as the water-soluble vitamin in the present invention, L-ascorbic acid or derivatives thereof are preferred because they require a relatively larger unit dose.

DETAILED DESCRIPTION OF THE INVENTION

The water-soluble vitamins used in the composition of the present invention include those generally used as medicines, foods, feeds, agricultural medicines and the like.

The water-soluble vitamins are both natural and synthetic, pure or substantially pure vitamins, or chemical derivatives and mixture thereof. For example, thiamine HCl, thiamine nitrate, riboflavin, pyridoxine HCl, nicotinamide, calcium pantothenate, folic acid, biotin, vitamin $B_{12}$, L-ascorbic acid, calcium L-ascorbate, sodium L-ascorbate, lipoic acid, inositol and the like are used alone or in combination.

The amount of the vitamin to be contained in the composition of the present invention can be appropriately selected according to particular kinds of the vitamins to be used. Normally, the vitamin content is in a range between about 90 to 99.8% by weight based on the total weight of the composition.

As indicated above, in the present invention, preferably, L-ascorbic acid or a derivative thereof, for example sodium L-ascorbate or calcium L-ascorbate is preferably used as the water-soluble vitamin. Although particle size is not specifically limited, as for particles of L-ascorbic acid to be used in the present invention, preferably, 60% or more of the particles can pass through a 200 mesh sieve. More preferably, 80% or more of particles can pass through a 200 mesh sieve and 50% or more of them can pass through a 325 mesh sieve. The term "mesh" used herein is that according to W. S. Tyler Standard. Powder to be used may be pulverized or may not be pulverized.

The polymer binder includes water-soluble cellulose (e.g., hydroxypropyl cellulose, hydroxymethyl cellulose, hydroxypropylmethyl cellulose, etc.), polymer compounds (e.g., polyvinyl pyrrolidone, polyvinyl alcohol, dextrin, pullulan, pregelatinized starch, gelatinized modified starch, gum arabic, gelatin, etc.) and the like. As for the organic solvent-soluble binders, for example, organic solvent-soluble cellulose materials (e.g., cellulose acetate phthalate, hydroxypropylmethyl cellulose phthalate, ethyl cellulose, etc.) can be used. Preferably, hydroxypropylmethyl cellulose, for example, that sold under the trade name of "TC-5" (manufactured by Shin-Etsu Chemical Co., Ltd.) and the like can be used.

In addition to the water-soluble vitamin and the polymer binder, at least one additive selected from the group consisting of monosaccharides, disaccharides, sugar alcohols, dextrin and organic acids is formulated in the composition of the present invention.

Examples of the monosaccharides and sugar alcohols thereof include L-arabinose, D-xylose, D-2-deoxyribose, D-ribose, D- and L-galactose, D-glucose, D-mannose, D-fructose, L-sorbose, L-fucose, L-rhamnose, D-glucosamine, D-sorbitol, D-mannitol, galactitol, erythritol and the like. Particularly, glucose is preferred.

Examples of disaccharides and sugar alcohols thereof include cellobiose, gentiobiose, isomaltose, kojibiose, lactose, lactitol, laminaribiose, maltose, melibiose, nigerose, sophorose, sucrose, paratinose, $\alpha,\alpha$-trehalose, Palatinit® (an equimolecular mixture of $\alpha$-D-glucopyranosyl-1,6-sorbitol and $\alpha$-D-glucopyranosyl-1,6-mannitol) and the like. Particularly, maltitol and lactitol are preferred.

The organic acids used in the present invention include aliphatic mono to tri-carboxylic acids such as citric acid, tartaric acid, malic acid, maleic acid, gluconic acid, sodium gluconate, potassium gluconate, and fumaric acid; uronic acids such as D-galacturonic acid, D-glucuronic acid, and D-mannuronic acid; and organic acids belonging to water-soluble vitamins such as L-ascorbic acid, D-iso-ascorbic acid, and sodium salts thereof; amino acids such as alanine, glycine, valine, leucine, isoleucine, serine, threonine, cysteine, cystine, methionine, aspartic acid, glutamic acid, lysin, arginine, phenylalanine, tyrosine, histidine, tryptophan, proline, oxyproline and glutamine. In view of problems such as coloring and the like, aliphatic carboxylic acids and uronic acids, and organic acids belonging to water-soluble vitamins are preferred than amino acids.

These additives can be used alone or in combination. They are used in such an amount that sum of the additives and the polymer binder is 0.2 to 10% by weight, preferably 0.6 to 5% by weight based on the total weight of the whole composition.

When the same component as the polymer binder such as dextrin is used as the additive, the component is used in such an amount that total amount of the component is within the above-indicated range. When the additive to be used corresponds to the water-soluble vitamin such as L-ascorbic acid or sodium salt thereof, it is preferred to weigh a portion of the water-soluble vitamin corresponding to that to be used as the additive, separately, and to add the portion together with the polymer binder, separately.

For producing the composition of the present invention, granulation is carried out, while coating the water-soluble vitamin with a solution of the polymer compound by per se known methods such as fluidized bed granulation, spray drying, kneading, rolling pan granulation. As indicated above, granulation can be carried out, while a mixture of the water-soluble vitamin and the additive is coated with a solution of the polymer binder. Alternatively, granulation can be carried out, while the water soluble vitamin is coated with a solution of the polymer binder and the additive.

Preferably, fluidized bed granulation method is employed. In this method, granulation is carried out by keeping a powder material in a fluidized state in a fluid (in many cases, in hot air) blowing up from a bottom part of a fluidized bed dryer and spraying the polymer compound. This granulation can be carried out with an apparatus by which granulation and drying can be done simultaneously, for example, Glart (Glart, Germany, sold by Ohgawara Seisakusho K.K.), Aeromatic, Multiplex (Aeromatic AG, Switzerland, sold by POWREX K.K.), Galmic (Galmic Engineering, U.S.A., sold by Itochu Shoji), Growmax (Fuji Powdal), Flowcorter, Spiralflow (Freund Sangyo) and the like.

In the present invention, as a solvent to be used for preparing a coating solution, there can be used a solvent which can dissolve the saccharides and polymer compounds to be added to the solution, for example, water, organic solvents [e.g., alcohols (e.g., methyl alcohol, ethyl alcohol, isopropyl alcohol), acetone, etc.] and the like. The concentration of the solvent can be selected from a practical view point, for example, about 1 to 20% by weight, preferably about 3 to 15% by weight.

A tablet having sufficient mechanical strength with retaining a high water-soluble vitamin content can be produced by mixing the granules of the composition of the present invention obtained by the above granulation with a lubricant, and compressing the mixture.

Other additives such as lubricants used for compressing can be added. The lubricants include those used in production of normal tablets such as stearic acid and its salts (magnesium stearate, calcium stearate and stearic acid), fatty acid sucrose esters, corn starch and the like. The amounts and kinds of the lubricants can be selected so that tablets having practical strength and disintegration properties can be obtained. Normally, the desirable amount is about 0.5 to 7% by weight based on the amount of the water-soluble vitamin, for example, L-ascorbic acid.

The table thus-obtained has the following mechanical strength. For example, when the granules containing 95% L-ascorbic acid as the water-soluble vitamin obtained by granulation with fluidized bed granulation is used, mechanical strength (hardness) of a tablet having 11.0 mm $\phi$, 8.5 R and 530 mg/tablet is such that its mechanical strength obtained at a compression pressure of 1.6 ton is not lower than that obtained at a compression pressure of 1.4 ton. That is, lowering of table strength due to compression problem is not caused even at a compression pressure of 1.6 ton and the tablet has a mechanical strength of 15 kp/cm$^2$ or more, preferably 20 kp/cm$^2$ or more, normally 20 to 35 kp/cm$^2$ as hardness (the value obtained by dividing a measurement by a cross section area) determined using a tablet hardness test apparatus (Schleuinger Model 6D).

On the other hand, in general, a tablet having higher mechanical strength (hardness) has a longer disintegration and dissolution time. The tablet obtained by compressing at a pressure of 1.4 ton has the following tablet properties. For example, the disintegration time measured by disintegration test using a disintegration test apparatus (NT-40HS, Toyama Sangyo K.K.) without an auxiliary plate is shorter than 20 minutes, normally shorter than 18 minutes. The tablet thus-obtained is also within the scope of the present invention.

Thus, according to the present invention, powder of the water-soluble vitamin can be uniformly coated with a small amount of the polymer compound, and a composition containing a higher amount of the water-soluble vitamin such as L-ascorbic acid can be obtained. For example, when the above amount of the lubricant is used for producing a tablet, a tablet containing about 90 to 99% by weight of L-ascorbic acid can be obtained and thereby a practically useful tablet containing about 50 to 2,000 mg/tablet of L-ascorbic acid can be obtained.

Moreover, according to the present invention, granules which scarcely contain finely divided particles but have excellent fluidity can be obtained. This is very convenient for handling and fine dusts are hardly generated. In addition, they can be served as a vitamin granule composition which exhibits excellent mixing property and stability upon formulating with other agents.

The following Experiments, Examples and Comparative Examples further illustrate the present invention in detail but are not to be construed to limit the scope thereof. All the "percents" and "parts" used in the Examples are by weight unless otherwise stated.

Experiment 1

Screening of additives

For obtaining additives effective for improving compression molding properties of L-ascorbic acid (hereinafter sometimes abbreviated as VC), various additives were screened.

Method

Tablets were produced under the following conditions granulation, sieving and/or milling and compression conditions and tablet hardness and disintegration time were determined. Tablet hardness was calculated by dividing a measurement (kp) of a hardness test apparatus by a cross section area of a tablet.

In this experiment, 95% of L-ascorbic acid and 3% of hydroxypropylmethyl cellulose (HPMC) as a binder were used, and, regarding the remaining 2% of an additive, the screening was carried out. As a control (Comparative Example 1), granules obtained by using 97% of L-ascorbic acid and 3% of HPMC (without additive) were used (i.e., L-ascorbic acid content of Comparative Example 1 and samples to be tested were different). Granules obtained by using 95% of L-ascorbic acid and 5% of HPMC (Comparative Example 2) were also used.

For adding an additive, the additive was dissolved in a solution for spraying in granulation (solution addition) was mainly employed. Namely, 20 g of the additive was dissolved in a gelatinized solution of 30 g of HPMC and 345 g of water and the solution was sprayed and 950 g of L-ascorbic acid was granulated by fluidized bed granulation. In this step, viscosity of the solution used for spraying was almost constant.

In addition, addition of the additive in the powder form without dissolution (powder addition) was also investigated with respect certain samples. Namely, 970 g of a powder mixture of 950 g of L-ascorbic acid and 20 g of the additive were granulated by fluidized bed granulation with a gelatinized solution of 30 g of HPMC and 345 g of water.

The conditions for operation, compression and disintegration test and the additives used were as follows:

Granulation conditions

Apparatus: Fluidized bed granulator FD-3S (POWREX K.K.)

Batch scale: 1.0 kg/batch

Components: L-ascorbic acid 950 g, HPMC 30 g and additives 20 g

Air supply: 0.5 $m^3$/min

Spray pressure: 1 $kg/cm^2$

Supply air temperature: 90° C.

Spray air rate: 60 Nl/min

Exhaust temperature: 32 to 37° C.

Drying temperature: 55° C.

Spray solution rate: 30 ml/min

Composition of granulated material and spray solution:

TABLE 1

| | Granulated material | | Spray solution | | |
|---|---|---|---|---|---|
| | Ascorbic acid | Additive | HPMC | Additive | Water |
| Solution addition | 950 g | — | 30 g | 20 g | 345 g |
| Powder addition | 950 g | 20 g | 30 g | — | 345 g |

Sieving or milling conditions

Apparatus: Power Mill (Showa Giken K.K.)

Mesh size: 16 mesh

Compression conditions

Apparatus/rotation: CLEANPRESS Correct 6 HUK (Kikusui Seisakusho K.K./40 rpm)

Punch-mortar/weight: 11.0 mm 4, 8.5R, 530 mg/tablet (500 mg VC/tablet)

Compression pressure: 1.4 ton and 1.6 ton

Lubricant: magnesium stearate 0.8%

Mixing: V-shape mixer, 10 min.

Measurement of tablet hardness

Apparatus: Schleuniger MODEL 6D

Estimation: average hardness (kp) of 10 tablets/average cross section area ($cm^2$) of 10 tablets Disintegration test conditions Apparatus: Disintegration test apparatus NT-40HS (Toyama Sangyo K.K.)

Method: according to Japanese Pharmacopoeia, the test was carried out by using respective 6 tablets (11.0 mm φ, 8.5 R, 530 mg/tablet) obtained at a compression pressure of 1.4 ton. An auxiliary plate was not used (37° C., water).

Results

The results are shown in Tables 2 and 3.

TABLE 2

Experiment 1: VC 95% screening
(in order of tablet hardness at a compression pressure of 1.6 ton)

| 2% Additive sugar, organic acid | Method of addition | Tablet hardness (kp/cm$^2$) 1.4* | 1.6* | Disintegration time (min) 1.4* |
|---|---|---|---|---|
| maltitol (disaccharide, sugar alcohol) | solution | 28.5 | 29.6 | 14.8 |
| lactitol (disaccharide, sugar alcohol) | solution | 27.7 | 29.3 | 15.1 |
| glucose (monosaccharide, hexose) | solution | 26.8 | 28.8 | 15.2 |
| L-alanine (amino acid) | solution | 26.4 | 28.2 | 16.2 |
| fructose (monosaccharide, hexose) | solution | 25.6 | 27.2 | 15.0 |
| mannose (monosaccharide, hexose) | solution | 26.1 | 27.2 | 16.2 |
| galactose (monosaccharide, hexose) | solution | 23.8 | 27.1 | 15.3 |
| potassium gluconate (monocarboxylic acid) | solution | 24.0 | 26.8 | 15.0 |
| sucrose (1) (disaccharide) | solution | 23.7 | 26.5 | 15.2 |
| gluconic acid (monocarboxylic acid) | solution | 24.0 | 26.2 | 13.1 |
| HPMC Comparative Example 2 | solution | 23.1 | 26.1 | 18.2 |
| glycine (amino acid) | solution | 24.6 | 26.0 | 14.2 |
| glucose, fructose (monosaccharide, hexose) | solution | 23.8 | 25.9 | 15.9 |
| maleic acid (1) (dicarboxylic acid) | solution | 22.2 | 25.9 | 12.0 |
| xylose (monosaccharide, pentose) | solution | 24.2 | 25.8 | 14.1 |
| sucrose (2) (disaccharide) | powder | 22.2 | 25.4 | 15.1 |
| sodium gluconate (monocarboxylic acid) | solution | 23.2 | 24.6 | 12.4 |
| nicotinamide | solution | 22.5 | 24.6 | 12.1 |
| paratinit (disaccharide, sugar alcohol) | solution | 23.5 | 24.6 | 15.7 |
| sodium glucuronate (uronic acid) | solution | 22.7 | 24.4 | 14.3 |
| paratinose (disaccharide) | solution | 22.5 | 24.2 | 14.0 |
| maltose (disaccharide) | solution | 24.7 | 24.0 | 12.7 |
| citric acid (tricarboxylic acid) | solution | 22.2 | 23.7 | 12.2 |
| tartaric acid (dicarboxylic acid) | solution | 25.8 | 23.4 | 11.8 |

*: compression pressure (ton/11.0 mm φ, 8.5 R, 530 mg/tablet)

TABLE 3

Experiment 1: VC 95% screening
(in order of tablet hardness at a compression pressure of 1.6 ton)

| 2% Additive sugar, organic acid | Method of addition | Tablet hardness (kp/cm$^2$) 1.4* | 1.6* | Disintegration time (min) 1.4* |
|---|---|---|---|---|
| lactose (disaccharide) | solution | 21.2 | 23.4 | 15.1 |
| arginine (amino acid) | solution | 21.3 | 23.2 | 14.4 |

TABLE 3-continued

Experiment 1: VC 95% screening
(in order of tablet hardness at a compression pressure of 1.6 ton)

| 2% Additive sugar, organic acid | Method of addition | Tablet hardness (kp/cm$^2$) 1.4* | 1.6* | Disintegration time (min) 1.4* |
|---|---|---|---|---|
| malic acid (dicarboxylic acid) | solution | 22.1 | 23.2 | 13.8 |
| trehalose (disaccharide) | solution | 23.2 | 23.1 | 11.8 |
| L-arabinose (monosaccharide, pentose) | solution | 22.5 | 23.0 | 14.6 |
| β-alanine (amino acid) | solution | 21.1 | 23.0 | 13.2 |
| Paindex No. 6 (dextrin) | solution | 20.3 | 22.8 | 13.1 |
| sodium ascorbate (ascorbic acid) | solution | 20.1 | 22.4 | 12.9 |
| glutamine (amino acid) | solution | 22.4 | 22.3 | 14.9 |
| D-isoascorbic acid (ascorbic acid) | solution | 19.6 | 22.1 | 16.0 |
| Paindex No. 1 (dextrin) | solution | 20.3 | 21.8 | 14.0 |
| galacturonic acid (uronic acid) | solution | 20.2 | 21.7 | 14.8 |
| threonine (amino acid) | solution | 20.8 | 21.7 | 13.2 |
| glucosamine HCl (amino sugar) | solution | 20.6 | 21.4 | 14.4 |
| maleic acid (2) (dicarboxylic acid) | powder | 18.8 | 21.4 | 12.2 |
| mannitol (monosaccharide, sugar alcohol) | solution | 19.2 | 20.9 | 15.1 |
| valine (amino acid) | solution | 20.2 | 20.8 | 12.8 |
| L-sorbose (monosaccharide, hexose) | solution | 19.6 | 20.8 | 13.3 |
| fumaric acid (dicarboxylic acid) | powder | 15.2 | 20.7 | 11.7 |
| erythritol (monosaccharide, sugar alcohol) | solution | 17.0 | 20.4 | 12.4 |
| Paindex No. 3 (dextrin) | solution | 21.3 | 20.1 | 15.0 |
| sorbitol (monosaccharide, sugar alcohol) | solution | 17.9 | 19.9 | 16.4 |
| ribose (monosaccharide, pentose) | solution | 19.5 | 19.1 | 15.6 |
| serine (amino acid) | solution | 17.7 | 18.8 | 13.0 |
| L-ascorbic acid (ascorbic acid) | solution | 18.6 | 17.6 | 14.3 |
| succinic acid (dicarboxylic acid) | powder | 19.3 | 14.1 | 17.4 |
| xylitol (monosaccharide, sugar alcohol) | solution | 11.8 | 12.9 | 13.7 |
| Without additive Comparative Example 1 | | 16.0 | 10.5 | 14.0 |

*: compression pressure (ton/11.0 mm φ, 8.5 R, 530 mg/tablet)

As shown in Tables 2 and 3, remarkable lowering of tablet hardness was observed in the sample of Comparative Example 1, without additive, at the compression pressure of 1.6 ton. The hardness was lower than that at the compression pressure of 1.4 ton. This is a phenomenon, so-called, in general, "capping", indicating that the compression in Comparative Example 1 is insufficient.

To the contrary, no lowering of tablet hardness was observed in case of using, for example, sucrose. For almost all the samples subjected to this screening, no lowering of tablet hardness was observed even at the compression pressure of 1.6 ton and, among them, some samples showed the same compressibility as or higher compressibility than that of Comparative Example 2 using 2% of HPMC, i.e., in which 5% of the binder was used. The sample obtained by adding 2% of ascorbic acid to a gelatinized solution of HPMC and subjecting to granulation contained 97% of ascorbic acid. Although this L-ascorbic acid content was the same as that of Comparative Example 1, improvement of compressibility was observed in the sample obtained by adding ascorbic acid corresponding to the 2% portion to the gelatinized solution and granulating.

Experiment 2

Effect in case of 97% of L-ascorbic acid content

In Experiment 1, L-ascorbic acid content of the screening sample was 95%, which was different from the 97% of L-ascorbic acid content of Comparative Example 1. Then, whether the similar effect of the additives could be observed was investigated in case of 97% of L-ascorbic acid content.

Method

The solution for spraying was composed of 20 g of HPMC, 10 g of glucose and 345 g of water. By using this solution, 970 g of VC was granulated in a fluidized bed. In Comparative Example 3, the solution for spraying was composed of 30 g of HPMC and 345 g of water and granulation was carried out according to the same manner. Conditions for granulation, compression and estimation were same as those in Experiment 1. Comparative Example 1 was the same as that in Experiment 1.

Results

The results are shown in Table 4.

TABLE 4

Experiment 2: Effect of VC 97% (cellulosic binders)

| | Tablet hardness (kp/cm$^2$) | | | Disintegration time (min) | |
| --- | --- | --- | --- | --- | --- |
| | 1.0* | 1.4* | 1.6* | 1.4* | |
| glucose added (VC 97% sample) | 16.5 | 24.2 | 26.2 | 12.1 | [Example 1] |
| without addition of glucose (VC 97% sample) | 13.6 | 16.0 | 10.5 | 14.0 | [Comparative Example 1] |

*: compression pressure (ton/11.0 mm φ, 8.5 R, 530 mg/tablet)

As shown in Table 4, remarkable lowering of tablet hardness in Comparative Example 1 at the compression pressure of 1.6 ton was observed, whereas the sample to which glucose was added (Example 1) showed very high tablet hardness under the same conditions.

Effect of addition of glucose is exhibited, preferably, within the range of 0.8 to 1.6%, when L-ascorbic acid content is 97%. When the amount of glucose is smaller, the effect is decreased and, when the amount of glucose is larger, the amount of the binder, HPMC to be added is decreased and granulation becomes difficult. This shows that functions of glucose is not a mere binder.

Experiment 3

Effect of pregelatinized starch in case of 97% of L-ascorbic acid content

The same experiment as that of Experiment 2 was carried out by using pregelatinized starch as the binder.

Method

The solution for spraying was composed of 20 g of pregelatinized starch (Amycol C, Nichiden Kagaku K.K.), 10 g of glucose and 345 g of water. By using this solution, L-ascorbic acid was granulated in a fluidized bed and then worked up according to the same manner as that in Experiment 2. In Comparative Experiment 3, granulation was carried out by using 970 g of L-ascorbic acid and 30 g of pregelatinized starch.

Results

The results are shown in Table 5.

TABLE 5

Experiment 3: Effect of 97% VC (starch binders)

| | Tablet hardness (kp/cm$^2$) | | | Disintegration time (min) | |
| --- | --- | --- | --- | --- | --- |
| | 1.0* | 1.2* | 1.3* | 1.0* | |
| glucose added (VC 97% sample) | 12.9 | 15.2 | 16.2 | 5.2 | [Example 2] |
| glucose not added (VC 97% sample) | 8.7 | 9.8 | 7.0 | 5.0 | [Comparative Example 3] |

*: compression pressure (ton/11.0 mm φ, 8.5 R, 530 mg/tablet)

As shown in Table 5, remarkable lowering of tablet hardness in Comparative Example 3 at the compression pressure of 1.6 ton was observed, whereas the glucose added sample (Example 2) showed high tablet hardness under the same conditions.

Experiment 4

Effect of wet-granulation method (kneading method)

In Experiments 1 to 3, improvement of compressibility by additives in fluidized bed granulation was shown. Then, whether the same effect could be obtained in wet-granulation method (kneading method) or not was investigated by using glucose.

Method

Four samples (Examples 3 and 4 and Comparative Examples 4 and 5) were prepared under the following conditions and compression molding properties were estimated. The treatment after sieving was the same as that in Experiment 1.

Sample:

| | Additive | VC | HPMC | Glucose | Water |
| --- | --- | --- | --- | --- | --- |
| Example 3 | glucose added (VC 95% sample) | 950 g | 30 g | 20 g | 70 g |
| Example 4 | glucose added (VC 97% sample) | 970 g | 20 g | 10 g | 80 g |
| Comparative Example 4 | not added (VC 97% sample) | 970 g | 30 g | — | 90 g |
| Comparative Example 5 | not added (VC 95% sample) | 950 g | 50 g | — | 90 g |

In any case, glucose was dissolved in water and then added.

Granulation conditions

Apparatus: AICOH MIXER (kneading machine, Aicohsha Seisakusho)

Premixing: 5 min. (6 r.p.m.) After premixing, water was added.

Mixing: 20 min. (6 r.p.m.)

Sieving: 14 mesh

Drying: fluidized bed granulator (for 5 min. after reached at 55° C.)

Results

The results are shown in Table 6.

TABLE 6

Experiment 4: Effect of kneading method

| | Tablet hardness (kp/cm$^2$) | | | Disintegration time (min) | |
|---|---|---|---|---|---|
| | 1.0* | 1.4* | 1.6* | 1.4* | |
| glucose added (VC 97% sample) | 9.2 | 13.6 | 14.1 | 12.1 | [Example 3] |
| glucose added (VC 95% sample) | 12.4 | 17.8 | 21.2 | 14.3 | [Example 4] |
| without addition 1 (VC 97% sample) | 8.1 | 10.6 | 10.7 | 13.5 | [Comparative Example 4] |
| without addition 2 (VC 95% sample) | 6.8 | 10.0 | 11.0 | 14.0 | [Comparative Example 5] |

*: compression pressure (ton/11.0 mm φ, 8.5 R, 530 mg/tablet)

As shown in Table 6, all the glucose added samples showed tablet hardness higher than the sample containing 5% of HPMC.

Experiment 5

Effect of mixing of additive with granules

Regarding sucrose which was proved to improve compressibility of L-ascorbic acid, whether difference in improvement of compressibility between when sucrose was added to the spray solution before granulation (sucrose was dissolved in a HPMC gelatinized solution) and when sucrose was added to granules after granulation (granulation was carried out using only HPMC and sucrose in a powder form was added with lubricant before compression) was observed or not was investigated.

Method

A granule sample to which sucrose was added (Example 5) was the same as that of in Experiment 1. Comparative Example 1 was the same as that of Experiment 1. A mixing was prepared by mixing 2% of sucrose with Comparative Example 1 before compression (Example 6).

Compression conditions and the like were the same as those in Experiment 1.

Results

The results are shown in Table 7.

TABLE 7

Experiment 5: Effect of mixing

| | Tablet hardness (kp/cm$^2$) | | | Disintegration time (min) | |
|---|---|---|---|---|---|
| | 1.0* | 1.4* | 1.6* | 1.4* | |
| granulation + 2% sucrose | 15.1 | 23.7 | 26.5 | | [Example 5] |
| mixing + 2% sucrose | 13.7 | 16.9 | 12.7 | | [Example 6] |
| without addition (VC 97% sample) | 13.6 | 16.0 | 10.5 | 14.0 | [Comparative Example 1] |

*: compression pressure (ton/11.0 mm φ, 8.5 R, 530 mg/tablet)

As shown in Table 7, the sample of Example 6 prepared by adding sucrose immediately after granulation did not show improvement of compressibility. It was found that the additive showed its effect when it was added before granulation.

Experiment 6

Effect of addition of glucose in vitamin B$_1$

Whether the improvement effect on compressibility by the additive observed in L-ascorbic acid was also observed in vitamin B$_1$ was investigated.

Method

Compressibility of a sample containing 95% vitamin B$_1$ (HPMC 3%, glucose 2%) (Example 7) was compared with that of Example 6 (97% sample, HPMC 3%). Granulation conditions and the like were the same as those in Experiment 1.

Results

The results are shown in Table 8.

TABLE 8

Experiment 6: Effect of addition of glucose in VB$_1$

| | Tablet hardness (kp/cm$^2$) | | Disintegration time (min) | |
|---|---|---|---|---|
| | 1.0* | 1.5* | 1.5* | |
| glucose added (VB$_1$ 95% sample) | 17.8 | 24.9 | 66.7 | [Example 7] |
| without addition (VB$_1$ 97% sample) | 11.8 | 17.6 | 58.6 | [Comparative Example 6] |

*: compression pressure (ton/11.0 mm φ, 8.5 R, 530 mg/tablet)

The same improvement effect on compressibility by addition of glucose as that observed in case of L-ascorbic acid was also observed in case of vitamin B$_1$ was observed.

Experiment 7

Effect of addition of glucose in vitamin B$_6$

Whether the improvement effect on compressibility by the additive observed in L-ascorbic acid was also observed in case of vitamin B$_6$ was investigated.

Method

Compressibility of a sample containing 95% of vitamin B$_6$ (HPMC 3%, glucose 2%) (Example 8) was compared with that of Example 7 (97% sample, HPMC 3%). Granulation conditions and the like were the same as those in Experiment 1.

Results

The results are shown in Table 9.

TABLE 9

Experiment 7: Effect of addition of glucose in case of VB$_6$

| | Tablet hardness (kp/cm$^2$) | | Disintegration time (min) | |
|---|---|---|---|---|
| | 1.0* | 1.5* | 1.5* | |
| glucose added (VB$_6$ 95% sample) | 25.9 | 30.8 | 11.2 | [Example 8] |
| without addition (VB$_6$ 97% sample) | 19.6 | 24.1 | 12.2 | [Comparative Example 7] |

*: compression pressure (ton/11.0 mm φ, 8.5 R, 530 mg/tablet)

The same improvement effect of compressibility by addition of glucose as that observed in case of L-ascorbic acid was also observed in case of vitamin B$_6$.

As described hereinabove, the composition of the present invention can be used in various art fields because the composition has excellent compressibility, in particular, upon preparing a tablet, it can provide a table having high mechanical strength (hardness) with less compression problem and easy disintegration.

What is claimed is:

1. An L-ascorbic acid composition which comprises about 90 to 99.8% by weight of L-ascorbic acid, hydroxypronylmethyl cellulose and at least one additive selected from the group consisting of maltitol, lactitol, glucose, L-alanine, fructose, mannose, galactose, potassium gluconate, sucrose, gluconic acid, sodium gluconate, nicotinamide, Palatinit®, sodium glucuronate, lactose and dextrin, obtained by carrying out granulation by a fluidized bed granulation method, while coating L-ascorbic acid with a solution of the polymer and the additive.

2. A process for producing a L-ascorbic acid composition comprising about 90 to 99.8% by weight of L-ascorbic acid, hydroxypropylmethyl cellulose and at least one additive selected from the group consisting of maltitol, lactitol, glucose, L-alanine, fructose, mannose, galactose, potassium gluconate, sucrose, gluconic acid, sodium gluconate, nicotinamide, Palatinit®, sodium glucuronate, lactose and dextrin, said process comprising carrying out granulation by a fluidized bed granulation method, while coating L-ascorbic acid with a solution of the polymer and the additive.

3. An L-ascorbic acid tablet obtained from the composition according to claim 1.

4. A composition according to claim 1, wherein the additive is dextrin.

* * * * *